United States Patent [19]

Eckler

[11] 4,410,746
[45] Oct. 18, 1983

[54] PREPARATION OF NITRO-OLEFINS

[75] Inventor: Paul E. Eckler, Terre Haute, Ind.

[73] Assignee: Angus Chemical Company, Northbrook, Ill.

[21] Appl. No.: 385,150

[22] Filed: Jun. 4, 1982

[51] Int. Cl.³ .............................................. C07C 76/02
[52] U.S. Cl. .................................................. 568/943
[58] Field of Search ............................... 568/943, 944

[56] References Cited

U.S. PATENT DOCUMENTS 3,240,823  3/1966  Bonetti et al. ...................... 568/942
3,255,263  7/1966  Abbott ................................ 568/943

OTHER PUBLICATIONS

Perkalin, Unsaturated Nitro Compounds, Daniel Davey & Co., N.Y. 1964, pp. 2, 16, 17 and 20 to 23.

Primary Examiner—Leland A. Sebastian
Attorney, Agent, or Firm—Leydig, Voit, Osann, Mayer & Holt, Ltd.

[57] ABSTRACT

A process for the preparation of nitro-olefins comprising reacting a compound of the formula

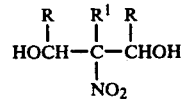

where R and R¹ can be hydrogen, alkyl of 1–20 carbon atoms or phenyl, with an aldehyde acceptor selected from the group consisting of alkylene polyols or aromatic polyols, in the presence of an alkaline catalyst or a Lewis acid catalyst.

7 Claims, No Drawings

PREPARATION OF NITRO-OLEFINS

This invention relates to a process for the preparation of nitro-olefins. In a particular aspect this invention relates to an improved process for the preparation of nitro-olefins from nitrodiols.

Nitro-olefins have been known for many years; Hass and Riley reviewed the literature on nitro-olefins in Chem. Rev. 32, 409–414 (1943) and according to them, E. Simon reported nitrostyrene in 1839 (Ann. 31, 269) while B. Priebs in 1884 reported the preparation of nitrostyrene by condensing benzaldehyde and nitromethane in the presence of zinc chloride (Ann. 225, 319–64). R. L. Hasche, U.S. Pat. No. 2,298,375 disclosed a process wherein a primary nitroalkane and formaldehyde are condensed in the vapor phase above 200° C. over a dehydrating catalyst impregnated with an acid or metallic oxides on alumina or silica gel. G. D. Buckley and C. W. Sciafe, J. Chem. Soc. (1947) 1471 reacted a nitroalcohol with phthalic anhydride.

Nitro-olefins are useful as pesticides, as disclosed by Bousquet et al, U.S. Pat. No. 2,335,384, and in the preparation of homopolymers and copolymers, e.g. as described by R. S. Sovish and W. Boettcher, J. Poly. Sci. Part A, Volume 2, 5247 (1964); M. H. Reich et al, U.S. Pat. No. 3,445,437 also disclosed a method for providing homopolymers of nitroalkylenes.

SUMMARY OF THE INVENTION

It is an object of this invention to provide a process for the preparation of nitro-olefins.

It is another object of this invention to provide a process for the preparation of nitro-olefins from nitrodiols.

Other objects of this invention will be obvious to those skilled in the art from the disclosure herein.

It is the discovery of this invention to provide a method for preparing nitro-olefins by reacting a dihydroxynitro compound with an aldehyde acceptor in the presence of a catalyst.

DETAILED DISCUSSION

The nitrodiols useful in the practice of this invention are aromatic-substituted or aliphatic compounds corresponding to the formula

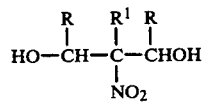

where R can be hydrogen, alkyl of 1–20 carbon atoms or aryl, e.g. phenyl. $R^1$ can be hydrogen, methyl or ethyl. The nitro-olefins thereby obtained correspond to the formula

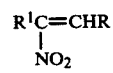

The preferred nitrodiols are those where R is hydrogen. More particularly, the preferred compounds are 2-nitro-2-methyl-1,3-propanediol; 2-nitro-2-ethyl-1,3-propanediol or 2-nitro-1,3-propanediol. As is known, nitrodiols are formed by condensation of a primary nitroalkane of the formula $$R^1CH_2NO_2$$

with a carbonyl compound, usually an aldehyde of the formula RCHO where R and $R^1$ have the same definitions as above. Preparation of suitable aryl or alkyl nitrodiols as raw materials for the preparation of nitro-olefins by the process of this invention is well within the skill of the ordinary artisan.

Aldehyde acceptors suitable for the practice of this invention include compounds capable of forming cyclic formals, such as polyols with 1,2 or 1,3 diol substitution. Typical polyols include but are not limited to glycols, e.g. alkylene glycols of 2–4 carbon atoms; triols, e.g. glycerol, trimethylolethane, trimethylolpropane and trimethylolbutane; pentaerythritol and the hexitols, e.g. sorbitol and mannitol, and polyvinyl alcohol. The amount of polyol used is generally about 1:1 molar hydroxy equivalent or more. In other words, when a glycol is used, it is present in about a 1:1 molar ratio or more. When a triol is used, it is present in at least about a 2:3 molar ratio. When a tetrol is used, it is present in at least about a 2:1 ratio or more, etc.

Catalysts suitable for the practice of this invention include metal salts, e.g. Lewis acids and certain inorganic alkaline compounds. Lewis acids useful as catalysts in the practice of this invention are known in the art. In general, they can be described as compounds which act as electron acceptors. Catalysts suitable for the practice of this invention include but are not limited to chloride salts such as those of magnesium, calcium, lithium, potassium, sodium, titanium (i.e.: the tetrachloride), iron (i.e. ferric chloride); also other salts such as magnesium nitrate, tetrabutyl titanate and tin compounds such as Fascat 4101 sold by M&T Chemicals Corporation, are suitable. However, magnesium sulfate and sulfonic acids were not effective.

Suitable alkaline catalysts (which would not be considered Lewis acids) include magnesium and calcium oxides, and sodium hydroxide.

The amount of catalyst used is generally about 6% based on the weight of the reactants. However, considerable departure from this figure can be made without departing from the concepts of this invention. Generally the lower the amount of catalyst the longer the reaction time.

The reaction is preferably conducted at an elevated temperature and advantageously in the presence of a solvent. Toluene and xylene are suitable solvents and when they are used, water of reaction can be removed by azeotropic distillation. A suitable temperature at atmospheric pressure is in the range of from about 150° C. to 227° C. Most of the product forms at about 200° C. Also, it is preferred to conduct the reaction under an oxygen-free atmosphere which can be provided by sweeping the reaction vessels with nitrogen and maintaining a nitrogen atmosphere throughout the reaction period.

The invention will be better understood with reference to the following examples. It is understood, however, that the examples are intended only to illustrate the invention, and it is not intended that invention be limited thereby.

EXAMPLE 1

Into a 250 ml, 3 neck flask equipped with magnetic stirring, thermometer and vacuum distillation column, there was delivered 65 g sorbitol (0.36 mole), 75 g 2- nitro-2-ethyl-1,4-propanediol (NEPD) (0.5 mole) and 5.0 g of magnesium chloride hydrate. The pressure was reduced to 50 mm and distillation was carried out at a vapor temperature of 50° C. The distillate was collected and extracted three times with diethylether. The ether extract was dried over anhydrous magnesium sulfate, then the ether portion was distilled. After removing the ether, the resulting product was distilled at 50 mm. There was obtained 2-nitro-1-butene.

EXAMPLE 2

The experiment of Example 1 was repeated in all essential details except that 2-nitro-2-methyl-1,3-propanediol 68 g was used as the nitrohydroxy compound. There was obtained 2-nitro-1-propene.

EXAMPLE 3

To the apparatus described in Example 1, there were delivered propylene glycol 11.4 g, NEPD 14.9 g and magnesium chloride hydrate 1.0 g. The mixture was heated at 150° C. for 5½ hours and the distillate was collected. 2-Nitro-1-butene was obtained.

EXAMPLE 4

The experiment of Example 3 was repeated in all essential details except that 25 ml xylene was added as a solvent. The reaction temperature was 138°–140° C. and the reaction was complete in about 3.5 hours. 2-Nitro-1-butene was obtained in good yield.

EXAMPLE 5

The experiment of Example 1 is repeated in all essential details except that it is carried out at ambient pressure. The pot temperature during the reaction is in the range of from 150° C. to 227° C. 2-Nitro-1-butene is obtained in good yield.

I claim:

1. A process for the preparation of nitro-olefins comprising reacting a nitrodiol with an aldehyde acceptor in the presence of a catalyst.

2. A process for the preparation of nitro-olefins comprising reacting a compound of the formula

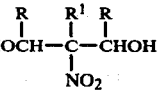

where R and R$^1$ can be hydrogen, alkyl of 1–20 carbon atoms or phenyl, with an aldehyde acceptor selected from the group consisting of alkylene polyols or aromatic polyols, in the presence of an alkaline catalyst or a Lewis acid catalyst.

3. The process of claim 2 wherein the aldehyde acceptor is selected from the group consisting of aliphatic polyols.

4. The process of claim 1 wherein the catalyst is a Lewis acid.

5. The process of claim 4 wherein the catalyst is magnesium chloride, calcium chloride, lithium chloride, potassium chloride, sodium chloride, aluminum chloride, ferric chloride or titanium tetrachloride.

6. The process of claim 4 wherein the catalyst is magnesium nitrate or tetrabutyl titanate.

7. The process of claim 1 wherein the catalyst is an alkali hydroxide or an alkaline earth oxide or hydroxide.

* * * * *